US00PP29165P3

(12) United States Plant Patent
Kordes

(10) Patent No.: US PP29,165 P3
(45) Date of Patent: Apr. 3, 2018

(54) HYBRID TEA ROSE PLANT NAMED 'KOROLIGEO'

(50) Latin Name: *Rosa hybrida*
Varietal Denomination: KORoligeo

(71) Applicant: W. Kordes Söhne Rosenschulen GmbH & Co. KG, Klein Offenseth-Sparrieshoop (DE)

(72) Inventor: Tim-Hermann Kordes, Klein Offenseth-Sparrieshoop (DE)

(73) Assignee: W. Kordes Söhne Rosenschulen GmbH & Co. KG, Klein Offenseth-Sparrieshoop (DE)

( * ) Notice: Subject to any disclaimer, the term of this patent is extended or adjusted under 35 U.S.C. 154(b) by 30 days.

(21) Appl. No.: 14/999,277

(22) Filed: Apr. 19, 2016

(65) Prior Publication Data

US 2017/0303451 P1 Oct. 19, 2017

(51) Int. Cl.
*A01H 5/02* (2006.01)

(52) U.S. Cl.
USPC ..... Plt./134
CPC ..... *A01H 5/0222* (2013.01)

(58) Field of Classification Search
USPC ..... Plt./134, 135, 136, 130, 133, 145, 141, Plt./144, 104, 102, 103
CPC ..... A01H 5/0222; A01H 5/0216; A01H 5/02; A01H 5/00
See application file for complete search history.

(56) References Cited

PUBLICATIONS

Greenheart Farms ELEGANZA Hybrid tea roses, retrieved on Jul. 10, 2017, retrieved from the Internet at <http://www.greenheartfarms.com/catalog/eleganzaroses/ohhappyday> 2 pp.*
New Plants and Flowers Results of French rose tials in Lyon 2012, retrieved on Jul. 6, 2017, retrieved from the Internet at <http://www.newplantsandflowers.com/results-of-french-rose-trials-in-lyon/> one page.*

* cited by examiner

*Primary Examiner* — June Hwu
(74) *Attorney, Agent, or Firm* — Samuel R. McCoy, Jr.

(57) ABSTRACT

'KORoligeo' is a new and distinct variety of *Rosa hybrida* which is characterized by the combination of an upright growth habit, medium green and semi-glossy foliage, excellent resistance to common rose diseases, and large, very-double pale yellow flowers borne in small clusters. The new variety propagates successfully by stem cuttings and grafting and has shown to be uniform and stable in the resulting generations from asexual propagation.

1 Drawing Sheet

Latin name of genus and species: The Latin name of the genus and species of the novel variety disclosed herein is *Rosa hybrida*.

Variety denomination: The inventive variety of *Rosa hybrida* disclosed herein has been given the variety denomination 'KORoligeo'.

PRIOR DISCLOSURES BY THE INVENTOR

The first public disclosure of the claimed plant was made on Jul. 24, 2015 at a public ceremony where cut stems of the instant variety were displayed by the inventor. 'KORoligeo' was not publically available or sold prior to one year before the date of the instant application.

BACKGROUND OF THE INVENTION

Parentage: The *Rosa hybrida* variety 'KORoligeo' is the result of a controlled cross-pollination breeding program carried out by the inventor in Klein Offenseth-Sparrieshoop, Germany. The objective of the said breeding program was to create a new and distinct rose plant with unique qualities, such as:

1. Uniform growth and flowering; and
2. Abundant, recurrent pale yellow flowers; and
3. Attractive and abundant foliage; and 4. Resistance to diseases encountered in landscapes and gardens.

This combination of qualities is not present in prior rose cultivars known to the inventor. These objectives have been substantially achieved and in that distinguish 'KORoligeo' from all other varieties known to the inventor.

'KORoligeo' is a seedling selection which resulted from the controlled pollination of *Rosa hybrida* 'POULduce' (patent abandoned), the seed parent, and *Rosa hybrida* 'KORacona' (not patented in the United States), the pollen parent, during the summer of 1999. As part of a rose development program, Tim-Hermann Kordes germinated seeds from the aforementioned hybridization during the following winter and conducted evaluations and observations on the resulting seedlings in a controlled environment in Klein Offenseth-Sparrieshoop, Germany. The resulting seedlings exhibited distinctive physical and biological characteristics. The new rose plant was selected as a single plant in May of 2000 from the seedling beds due to its superior characteristics and asexually propagated for further evaluation. This new and distinctive rose variety was given the name 'KORoligeo'.

Asexual Reproduction: 'KORoligeo' was first asexually propagated by bud grafting in July of 2000 at the inventor's nursery in Klein Offenseth-Sparrieshoop, Germany. Subsequently, 'KORoligeo' has been successfully propagated by stem cuttings and bud grafting in Jackson County, Oreg. These initial and other subsequent propagations conducted in controlled environments demonstrate that 'KORoligeo' reproduces true to type in successive generations of asexual reproduction.

SUMMARY OF THE INVENTION

The following characteristics have been repeatedly observed and represent the distinguishing characteristics of the new *Rosa hybrida* cultivar 'KORoligeo'. These traits, in combination, distinguish 'KORoligeo' as a new and distinct cultivar.

1. *Rosa hybrida* 'KORoligeo' exhibits an upright growth habit; and
2. *Rosa hybrida* 'KORoligeo' exhibits medium green and semi-glossy foliage; and
3. *Rosa hybrida* 'KORoligeo' exhibits excellent resistance to black spot disease and powdery mildew; and
4. *Rosa hybrida* 'KORoligeo' exhibits pale yellow flowers borne both solitarily and in small clusters, held upright; and
5. *Rosa hybrida* 'KORoligeo' exhibits very-double flowers of large size for a hybrid tea rose.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORoligeo', taken from a one year old plant.

DETAILED BOTANICAL DESCRIPTION

The following is a detailed botanical description of a new and distinct variety of *Rosa hybrida* known as 'KORoligeo', based upon observations made in September of 2014 from two year old plants grown outdoors in Jackson County, Oreg. Those skilled in the art will appreciate that certain characteristics will vary with older or, conversely, with younger plants. 'KORoligeo' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2001 edition except where common terms of color are used.

A botanical description of 'KORoligeo' and comparisons with other varieties of *Rosa hybrida* are provided below.

General plant description:

*Commercial classification*.—Hybrid tea rose.

*Growth rate*.—Moderately vigorous.

*Growth habit*.—Upright.

*Mature dimensions*.—135 cm tall and 75 cm wide, on average, when grown as a field plant.

*Cold hardiness*.—Grown successfully in USDA Hardiness Zones 7.

*Propagation*.—Stem cuttings and bud grafting.

*Disease resistance*.—Excellent resistance to Powdery mildew (*Sphaerotheca pannosa* var. *rosae*), black-spot (*Diplocarpon rosae*), rust (both *Phragmidium mucronatum* and *T. tuberculatum*), and *Botrytis* (*Botrytis cinerea*) diseases under normal growing conditions in Jackson County, Oreg.

Root system: Fibrous.

Stems:

*Stem color*.—Young stems are Yellow-Green Group 146D; mature stems are Yellow-Green Group 146C.

*Anthocyanin intonations*.—Greyed-Purple Group 184A intonations are primarily present on young stems.

*Stem surface texture*.—Both young stems and mature stems are smooth.

*Stem dimensions*.—Typical mature stems are approximately 40 cm long and 5 mm in diameter.

*Prickles*.—Incidence — Typically 7 to 10 prickles per 10 cm of stem, on average. Size — Average length is 5 to 8 mm long. Immature prickle color — Yellow-Green Group 145A. Mature prickle color — Greyed-Yellow Group 160B. Anthocyanin intonations — Intonations of Greyed-Purple Group 183C are primarily present on immature prickles and minimally present on the apices and bases of mature prickles.

*Shape*.—Deeply concave.

Leaves:

*Arrangement*.—Imparipinnate compound leaves; mature axillary leaves normally with 7 leaflets.

*Attachment*.—Petiolate.

*Dimensions*.—130 to 170 mm long and 90 to 110 mm wide.

*Abundance*.—Average.

*Stipules*.—Size — 15 to 20 mm long and 7 to 8 mm wide. Stipule color — Yellow-Green Group 146B; 146C on the midrib. Anthocyanin intonations — Intonations of Greyed-Purple Group 183C are minimally present on stipitate glands on the margins. Stipitate glands — Abundant on the margins. Margins — Glandular toothed. Texture, adaxial surfaces — Glabrous. Texture, abaxial surfaces — Glabrous. Apex — Apiculate. Base — Winged.

*Petiole*.—Dimensions — 20 to 25 mm long and 1.5 to 2.0 mm in diameter. Petiole color, adaxial surface — Yellow-Green Group 146B. Petiole color, abaxial surface — Yellow-Green Group 144A. Anthocyanin intonations — Minimal intonations of Greyed-Purple Group 183B are present on stipitate glands and at the point of leaf attachment. Margins — Limited number of stipitate glands present. Prickles — Occasionally one prickle is present at the point of leaf attachment. Stipitate glands — A limited number of stipitate glands are present on the margins only. Texture — Glabrous.

*Rachis*.—Length — Average 15 to 30 mm. Diameter — Average 1 to 2 mm. Color — Yellow-Green Group 144A. Anthocyanin intonations — Intonations of Greyed-Purple Group 183B are present at the point of leaf attachment only. Margins — Entire, with stipitate glands. Prickles — A few small prickles. Stipitate glands — A limited number of stipitate glands are present on the margins only. Surfaces — Glabrous underneath and papillate above.

*Leaflets*.—Dimensions — Average size of the terminal leaflet is 60 to 70 mm long and 35 to 45 mm wide. Shape — Elliptic. Apex — Acute. Base — Obtuse.

Margins — Serrated; not undulated. Luster and texture, adaxial surface — Semi-glossy and leathery. Luster and texture, abaxial surface — Matte and leathery. Juvenile foliage color, adaxial surface — Yellow-Green Group 144A. Juvenile foliage color, abaxial surface — Yellow-Green Group 147C. Mature foliage color, adaxial surface — Yellow-Green Group 147A. Mature foliage color, abaxial surface — Yellow-Green Group 148B. Anthocyanin intonations — Intonations of Greyed-Purple Group 184A cover the juvenile foliage; these same intonations are present on the margins, and abaxial surface of the mature foliage. Venation — Reticulate. Petiolule — Dimensions — 3 mm long and 1 mm wide. Petiolule color, adaxial surface — Green-Yellow Group 147D. Petiolule color, abaxial surface — Green-Yellow Group 147C. Anthocyanin intonations — Intonations of Greyed-Purple Group 185A are present throughout the juvenile foliage. These intonations are much more pronounced on the adaxial surface of the juvenile foliage and on juvenile growth in the spring. Prickles — None. Pubescence, adaxial and abaxial surfaces — None. Margins — Very limited number of stipitate glands.

Inflorescence:

*Inflorescence type.*—Panicles with generally 1 to 3 flowers which are held upright.

*Blooming habit.*—Recurrent.

*Size.*—25 cm high and 15 cm wide, on average.

*Peduncle.*—Length — 15 to 100 mm average length. Diameter — 3 to 5 mm average diameter. Color — Yellow-Green Group 144A. Anthocyanin intonations — Intonations of Greyed-Purple Group 183A. Strength — Strong. Surface — Glabrous; stipitate glands present.

Flowering laterals: Present below the initiation of inflorescence. Generally 3 to 6 flowering laterals are present, with 1 to 4 flowers per flowering shoot. The length of flowering laterals varies but typically reaches the same height as the central flower of the inflorescence, creating a bouquet appearance for each flowering stem.

Bud:

*Bud form.*—Long; pointed ovoid.

*Size.*—Upon opening, 25 to 30 mm in length from base of receptacle to distal end of bud and 15 to 20 mm diameter at its widest point.

*Texture.*—Smooth.

*Color, as sepals first unfold.*—Yellow Group 11D, with intonations of Red-Purple Group 58A.

*Color when one-quarter open, inner side.*—Marginal zone — White Group 155A. Middle zone — White Group 155A. Basal zone — Yellow Group 12B.

*Color when one-quarter open, outer side.*—Marginal zone — White Group 155A. Middle zone — White Group 155A. Basal zone — Yellow Group 12C.

*Guard petals.*—White Group 155A, with intonations of Red-Purple Group 58A; Yellow-Green Group 144A is present along the midrib.

Flower:

*Pedicels.*—Surface — A few fine hairs and a limited number of stipitate glands are present. Length — 50 to 80 mm, on average. Diameter — 2 to 3 mm, on average. Color — Yellow-Green Group 146C. Anthocyanin intonations — Greyed-Purple Group 183A. Strength — Strong. Texture — Papillate.

*Calyx.*—General — Comprised of five polysepalous sepals, with weak foliaceous appendages present on three of the five sepals. Sepals — Color, upper surface — Yellow-Green Group 146B. Color, lower surface — Yellow-Green Group 146B, with Yellow-Green Group 146D on the midrib and base. Anthocyanin intonations — Greyed-Purple Group 184A. Size — 30 to 40 mm long and 10 to 12 mm wide, on average. Apex — Typically apiculate and occasionally cirrose. Base — Flat at union with receptacle. Quantity — Five. Upper surface — Hoary. Lower surface — Leathery. Stipitate Glands — Limited number of stipitate glands present on margins. Margins — Cilliate.

*Corolla.*—Shape of corolla when viewed from the side — Upon opening, upper portion — Flattened convex. Upon opening, lower portion — Flat. Open flower, upper portion — Flat. Open flower, lower portion — Flat. Dimensions — Large size for a hybrid tea rose. When open, the average flower diameter is 85 to 100 mm and the average flower height is 30 to 40 mm. Fragrance — Light. Duration — On the plant for 5 to 7 days; as a cut flower, flowers will last 3 to 4 days. Senesced petals drop away cleanly. Petals — Petal count — Exhibits very-double flowers with an average of 50 to 55 petals under normal conditions. Petal arrangement — Quartered rosette. Petal reflex — Petals are somewhat reflexed. Timing of petal reflex — Petals begin to reflex upon opening; reflexing becomes more pronounced as the flower ages. Petal margin — Entire. Petal shape — Obovate. Apex — Obtuse. Base — Cuneate. Dimensions — 30 to 50 mm long and 20 to 45 mm wide. Texture, inner and outer surfaces — Smooth. Petal color, upon opening — Outermost petals, inner surface — Marginal zone — White Group 155A. Middle zone — Yellow Group 2D. Basal zone — Yellow Group 12B. Outermost petals, outer surface — Marginal zone — White Group 155A. Middle zone — White Group 155A. Basal zone — Yellow Group 13B. Innermost petals, inner surface — Marginal zone — Yellow Group 8B. Middle zone — Yellow Group 8A. Basal zone — Yellow Group 8A. Innermost petals, outer surface — Marginal zone — Yellow-Orange Group 15C. Middle zone — Yellow-Orange Group 15C. Basal zone — Yellow-Orange Group 15C. Basal petal spots, upon opening — Outermost petals — Color, inner surface — Yellow Group 12A. Color, outer surface — No distinct petal spot. Dimensions — 5 mm wide and 6 mm tall. Innermost petals — Color, inner surface — Yellow Group 12A. Color, outer surface — Yellow Group 12A. Dimensions — 20 mm wide and 30 mm tall. Petal color, after opening — Outermost petals, inner surface — Marginal zone — White Group 155A. Middle zone — White Group 155A. Basal zone — Green-Yellow Group 1D. Outermost petals, outer surface — Marginal zone — White Group 155C. Middle zone — White Group 155A. Basal zone — Yellow Group 4D. Innermost petals, inner surface — Marginal zone — Yellow Group 10C. Middle zone — Yellow Group 10C. Basal zone — Yellow Group 10A. Innermost petals, outer surface — Marginal zone — Yellow Group 10C. Middle zone —

Yellow Group 10C. Basal zone — Yellow Group 10A. Basal petal spots, after opening — Outermost petals — Color, inner surface — Yellow Group 12A. Color, outer surface — Yellow Group 12B. Dimensions — 7 to 8 mm wide and 6 to 8 mm tall. Innermost petals — Color, inner surface — Yellow Group 12A. Color, outer surface — Yellow Group 12A. Dimensions — 4 mm wide and 4 mm tall. General Tonality — On open flower, Yellow Group 11A to 11B. No change in general tonality at the end of the fourth day; thereafter the general tonality is White Group 155B. Petaloids — Quantity — 10 petaloids per flower, on average. Dimensions — Approximately 15 to 20 mm long and 5 to 15 mm wide. Color, inner surface — Yellow Group 10A. Color, outer surface — Yellow Group 10B. Margins — Entire. Shape — Irregular; obovate. Apex — Obtuse. Base — Attenuate. Texture, inner and outer surfaces — Smooth.

Reproductive organs:

*Stamens*.—Quantity — Approximately 100, on average; regularly arranged around the styles. Anthers — Shape — Ovoid. Dimensions — 2 to 4 mm long and 1 mm wide, on average. Color — Greyed-Yellow Group 162A. Pollen — Generally present. Color is Greyed-Orange Group N163C. Filaments — Color — Yellow Group 13B. Length — 5 to 10 mm.

*Pistils*.—Quantity — Abundant; approximately 120. Stigmas — Dimensions — 1.5 mm long and 1.0 mm wide. Location — Generally slightly superior in position to anthers. Color — Yellow-Orange Group 22B. Styles — Length — Approximately 8 mm long. Color — Greyed-Yellow Group 160B, with intonations of Red Group 39A.

*Ovary*.—Dimensions — 8 mm long and 5 mm wide. Color — White Group 155B.

*Receptacle*.—Shape — Funnel-shaped to urn-shaped. Dimensions — Approximately 8 to 10 mm high and 8 to 10 mm wide. Surface — Glabrous and glaucous. Color — Yellow-Green Group 144A, with intonations of Greyed-Purple Group 183A.

Hips and seed formation: Not observed to date.

COMPARISONS WITH THE PARENTS

The new rose plant may be distinguished from its seed parent, a *Rosa hybrida* 'POULduce', by the following combination of characteristics:

1. 'KORoligeo' exhibits flowers borne both solitarily and in small clusters, whereas 'POULduce' exhibits mostly solitary flowers.
2. 'KORoligeo' exhibits high disease resistance, whereas 'POULduce' exhibits average resistance.

The new rose plant may be distinguished from its pollen parent, *Rosa hybrida* 'KORacona', by the following combination of characteristics:

1. 'KORoligeo' exhibits pale yellow flowers, whereas 'KORacona' exhibits pink flowers.
2. 'KORoligeo' exhibits large flowers for a hybrid tea rose, whereas 'KORacona' exhibits medium size flowers.
3. 'KORoligeo' exhibits a very double petal count, whereas 'KORacona' exhibits a semi-double petal count.

COMPARISON WITH THE MOST SIMILAR *ROSA* CULTIVAR KNOWN TO THE INVENTOR

For a comparison, several physical characteristics of the *Rosa hybrida* variety 'KORaruli', a rose variety from the same inventor which is described and illustrated in U.S. Plant Pat. No. 22,352, are compared to 'KORoligeo' in Chart 1.

CHART 1

| Characteristic | 'KORoligeo' | 'KORaruli' |
|---|---|---|
| Coloration of the adaxial surface of mature foliage. | Yellow-Green Group 147A. | Green Group 136B. |
| Average petal count, at anthesis. | 50 to 55 petals. | 45 petals. |
| Number of leaflets per leaf. | Mature axillary leaves normally with 7 leaflets. | Mature axillary leaves normally with 5 leaflets. |

That which is claimed:

1. A new and distinct variety of rose plant named 'KORoligeo', as described and illustrated herein.

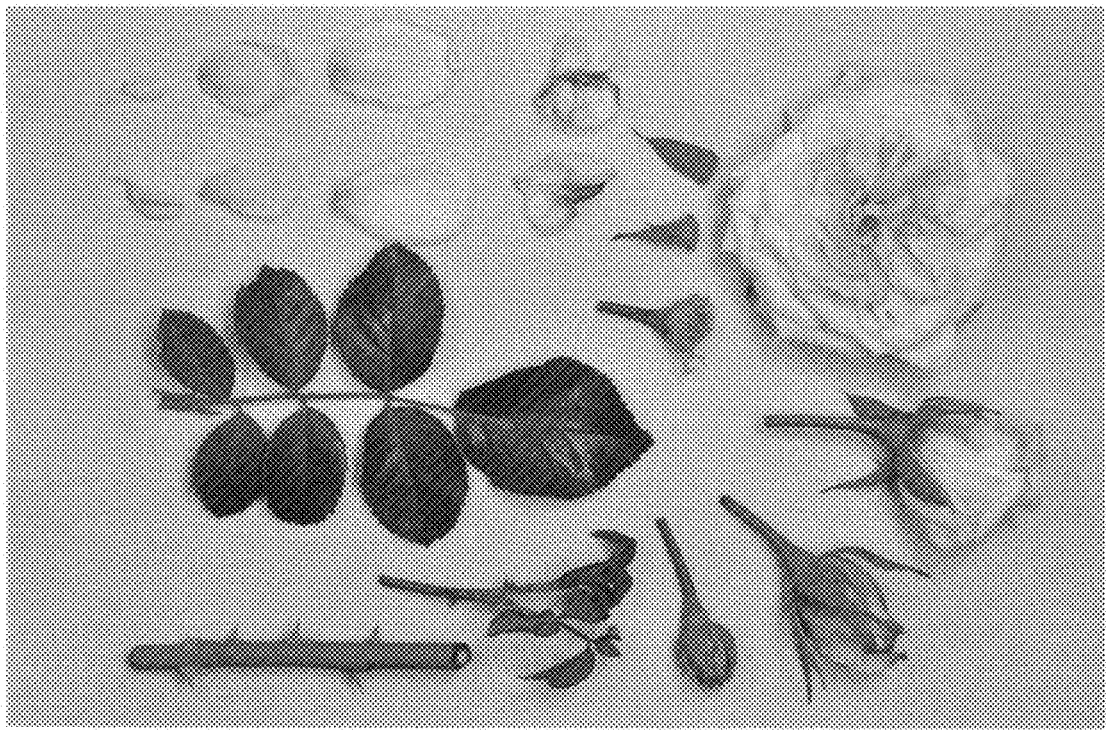

* * * * *